(12) United States Patent
Griffin et al.

(10) Patent No.: US 9,830,127 B1
(45) Date of Patent: Nov. 28, 2017

(54) ELECTROLARYNX CONTROL BUTTON ARRANGEMENT WITH IMPROVED FREQUENCY CONTROL

(71) Applicants: Clifford Jay Griffin, Murrieta, CA (US); Mark Andrew Robertson, Murrieta, CA (US)

(72) Inventors: Clifford Jay Griffin, Murrieta, CA (US); Mark Andrew Robertson, Murrieta, CA (US)

(73) Assignee: Griffin Laboratories (a California corporation), Temecula, CA (US)

( * ) Notice: Subject to any disclaimer, the term of this patent is extended or adjusted under 35 U.S.C. 154(b) by 0 days.

(21) Appl. No.: 15/244,003

(22) Filed: Aug. 23, 2016

Related U.S. Application Data

(63) Continuation-in-part of application No. 15/043,516, filed on Feb. 13, 2016, now Pat. No. 9,561,099.

(51) Int. Cl.
*A61F 2/20* (2006.01)
*G06F 3/16* (2006.01)

(52) U.S. Cl.
CPC ............. *G06F 3/165* (2013.01); *A61F 2/20* (2013.01); *A61F 2/203* (2013.01); *A61F 2002/206* (2013.01)

(58) Field of Classification Search
CPC ....... A61F 2/20; A61F 2002/206; A61F 2/203
USPC ........................................................... 381/70
See application file for complete search history.

(56) References Cited

U.S. PATENT DOCUMENTS

| | | | | |
|---|---|---|---|---|
| 4,685,448 A | * | 8/1987 | Shames | A61F 5/58 128/905 |
| 5,812,681 A | * | 9/1998 | Griffin | A61F 2/20 381/70 |
| 6,252,966 B1 | | 6/2001 | Griffin | |
| 9,031,249 B1 | | 5/2015 | Griffin | |
| 9,116,539 B1 | | 8/2015 | Griffin | |
| 2003/0031326 A1 | * | 2/2003 | Lukacovic | A61F 2/20 381/70 |
| 2011/0275412 A1 | * | 11/2011 | Khawand | G06F 3/04847 455/566 |
| 2015/0363012 A1 | * | 12/2015 | Sundara-Rajan | G06F 3/038 345/179 |

* cited by examiner

*Primary Examiner* — Disler Paul
(74) *Attorney, Agent, or Firm* — Loyal McKinley Hanson

(57) ABSTRACT

An electrolarynx includes a case housing tone-producing circuitry, a power switch to turn on the circuitry, a control button (i.e., a pushbutton) to actuate the power switch, and a pressure-sensitive-resistor (PSR) that is physically coupled to the pushbutton. The tone-producing circuitry is configured to respond to variations in PSR resistance that are caused by a user depressing the pushbutton. User-selected modes, that are selectable in one embodiment with a mode switch, include multiple frequency-varying modes (FVMs) in which the frequency of the electrolarynx tone is varied with different sensitivities to variations in PSR resistance, and multiple volume-varying modes (VVMs) for varying the volume of the electrolarynx tone with different sensitivities. A preferred embodiment provides a nonlinear frequency characteristic that facilitates operation at the low end of the pushbutton-controlled (i.e., PSR-controlled) frequency range, accomplishing same by applying suitable shape factors to frequencies of a linear frequency characteristic.

17 Claims, 8 Drawing Sheets

$$K = 100 * \left[ \frac{10^{(\log_{10}(X) \, * \, 10^{(Scale)})}}{10^{(\log_{10}(16) \, * \, 10^{(Scale)})}} \right]$$

where X = Button Pressure Increment, and
Scale = Desired Amount of Nonlinearity.

Equation 1

Fig. 7

TABLE A

| Force On PSR P | ADC Voltage $V_{IN}$ | Adjusted Voltage $V_{ADJ}$ | Linear Hertz $F_L$ | Shape Factor K | Shaped Voltage $V_K$ | Shaped Hertz $F_K$ |
|---|---|---|---|---|---|---|
| 0 | 1.65 | 0.00 | 50.00 | 0.00 | 0.0000 | 50.00 |
| 1 | 1.75 | 0.10 | 62.50 | 0.02 | 0.0000 | 50.00 |
| 2 | 1.86 | 0.21 | 75.00 | 0.14 | 0.0003 | 50.03 |
| 3 | 1.96 | 0.31 | 87.50 | 0.50 | 0.0016 | 50.19 |
| 4 | 2.06 | 0.41 | 100.00 | 1.25 | 0.0051 | 50.62 |
| 5 | 2.17 | 0.52 | 112.50 | 2.53 | 0.0130 | 51.58 |
| 6 | 2.27 | 0.62 | 125.00 | 4.50 | 0.0278 | 53.37 |
| 7 | 2.37 | 0.72 | 137.50 | 7.32 | 0.0529 | 56.41 |
| 8 | 2.48 | 0.83 | 150.00 | 11.17 | 0.0922 | 61.17 |
| 9 | 2.58 | 0.93 | 162.50 | 16.21 | 0.1505 | 68.24 |
| 10 | 2.68 | 1.03 | 175.00 | 22.62 | 0.2333 | 78.28 |
| 11 | 2.78 | 1.13 | 187.50 | 30.58 | 0.3469 | 92.04 |
| 12 | 2.89 | 1.24 | 200.00 | 40.26 | 0.4983 | 110.39 |
| 13 | 2.99 | 1.34 | 212.50 | 51.86 | 0.6953 | 134.27 |
| 14 | 3.09 | 1.44 | 225.00 | 65.56 | 0.9465 | 164.72 |
| 15 | 3.20 | 1.55 | 237.50 | 81.54 | 1.2613 | 202.89 |
| 16 | 3.30 | 1.65 | 250.00 | 100.00 | 1.6500 | 250.00 |

Fig. 8

ELECTROLARYNX CONTROL BUTTON ARRANGEMENT WITH IMPROVED FREQUENCY CONTROL

CROSS REFERENCE TO RELATED APPLICATIONS

This application is a continuation in part of U.S. patent application Ser. No. 15/043,516 filed Feb. 13, 2016 (i.e., the parent application), which parent application claims the benefit of U.S. Provisional Patent Application Ser. No. 62/273,319 filed Dec. 30, 2015.

BACKGROUND OF THE INVENTION

1. Technical Field

This invention relates generally to the electromechanical speech aids commonly referred to as artificial larynxes and as electrolarynxes, and more particularly to an improved electrolarynx construction with increased functionality.

2. Description of Related Art

A person without normal use of their vocal cords or larynx often uses an electrolarynx to speak. The electrolarynx includes a sound-producing component that delivers an electrolarynx tone (e.g., a buzzing sound) having a fundamental frequency in the speech range of the average human voice. To speak, the user introduces this artificially generated tone into a resonant speech cavity (i.e., the mouth, nose, or pharynx). While doing so, the user modulates the electrolarynx tone by varying the shape of the resonant speech cavity and by making the usual tongue, teeth, and lip constrictions so as to articulate the modulated tone as human speech.

U.S. Pat. Nos. 5,812,681; 6,252,966; 9,031,249; and U.S. Pat. No. 9,116,539 issued to Clifford J. Griffin describe some existing electrolarynxes. Each of those electrolarynxes typically includes a four-inch to five-inch long case that houses an electronic circuit board, a battery, an electro-mechanical transducer for producing vibrations (i.e., the electrolarynx tone), a volume control, and a power switch. The user grasps the case in one hand, actuates the power switch and volume control, and then presses the transducer portion of the electrolarynx against the outside of their throat so that electrolarynx tone vibrations travel through the throat tissues and into the mouth and throat for modulation and articulation.

One such electrolarynx includes a pressure-sensitive resistor (PSR) coupled to a pushbutton; the user depresses the pushbutton with their thumb to actuate the power switch while varying the pressure on the PSR (often referred in the alternative as a force-sensitive resistor, or FSR). The PSR is connected to electronic circuitry that varies the frequency of the electrolarynx tone according to changes in the amount of pressure (i.e., force) applied to the PSR. That way, the pushbutton-PSR combination enables both electrolarynx power-on and frequency variation of the electrolarynx tone with minimal, unnoticeable movement of the user pressing the pushbutton. Operation is somewhat easy, and a wide and continuous range of frequencies allows for increased control and subtle voice inflection, including syllable-specific intonation which may be used to approximate regionally specific or country specific voice patterns. Nevertheless, variation of elctrolarynx volume and careful frequency control at the low end of the pushbutton-controlled frequency range can be somewhat challenging.

SUMMARY OF THE INVENTION

In view of the foregoing, it is a primary objective of the present invention to provide an electrolarynx having significant improvements and increase functionality, including ease of both frequency and volume variation and ease of frequency control at the low end of the pushbutton-controlled frequency range. The "mode switch aspect" of the present invention helps achieve the above objective by providing an electrolarynx that enables a user to select which electrolarynx tone attribute is affected by variations in the resistance of the PSR. The user simply operates a mode switch on the electrolarynx to select a desired one of multiple modes of electrolarynx operation. In addition, the "nonlinear frequency characteristic aspect" of the present invention improves upon the foregoing by providing a nonlinear relationship between force on the pushbutton (i.e., force on the PSR) and frequency of the electrolarynx tone in order to thereby improve frequency control at the low end of the pushbutton-controlled frequency range.

To paraphrase some of the more precise language developed herein for the mode switch aspect of the present invention, an electrolarynx constructed according to the mode switch aspect of the present invention includes an enhanced, multimode pushbutton-PSR arrangement. The electrolarynx includes (i) a case, (ii) tone-producing circuitry on the case for producing an electrolarynx tone having a frequency and a volume, (iii) a power switch on the case for turning on power to the tone-producing circuitry, (iv) a pushbutton on the case that is operatively connected to the power switch for purposes of enabling a user to activate the power switch, and (v) a PSR physically coupled to the pushbutton so that the PSR resistor has a resistance value dependent on the pressure a user applies to the pushbutton.

According to the mode switch aspect invention, the tone-producing circuitry is configured to operate in multiple user-selected modes of electrolarynx operation. In a first frequency-varying mode (i.e., a first FVM), the tone-producing circuitry varies the frequency of the electrolarynx tone according to variations in the PSR resistance value. In a first volume-varying mode (i.e., a first VVM), the tone-producing circuitry varies the volume. A mode switch component of the electrolarynx enables the user to set a user-selected mode of operation. Preferably, additional modes of operation are included, some of which vary sensitivity to changes in the PSR resistance value.

According to the nonlinear frequency characteristic aspect of the present invention, the tone-producing circuitry varies the pushbutton-controlled frequency of the electrolarynx tone as a nonlinear function of the force applied to the pushbutton (i.e., a nonlinear function of the PSR resistance value). Less sensitivity to applied force at the low end of the pushbutton-controlled frequency range results, thereby facilitating low frequency adjustments by a user who is only lightly pressing the pushbutton.

Thus, the present invention provides an electrolarynx having significant improvements and increase functionality, including ease of both frequency and volume variation using a single pushbutton-PSR combination, and a nonlinear frequency characteristic that is achieved, in one form of the invention, with a shaping factor saved in a logarithmic lookup table. The following illustrative drawings and

BRIEF DESCRIPTION OF THE DRAWINGS

FIG. 7 is a sample Equation 1 for calculating shaping factors for the desired nonlinear frequency characteristics; and FIG. 8 is a "Table A" that provides sample "button pressure versus tone frequency" data for both linear and nonlinear frequency characteristics.

DESCRIPTION OF THE PREFERRED EMBODIMENTS

The following description proceeds by describing the mode switch aspect of the present invention in a first section entitled "Mode Switch." The description continues thereafter by describing the nonlinear frequency characteristic aspect in a second section entitled "Nonlinear Frequency Characteristic." A reader of this description who is already familiar with the mode switch description of the present invention may choose to proceed directly to the "Nonlinear Frequency Characteristic" section.

Mode Switch.

Figure 1:
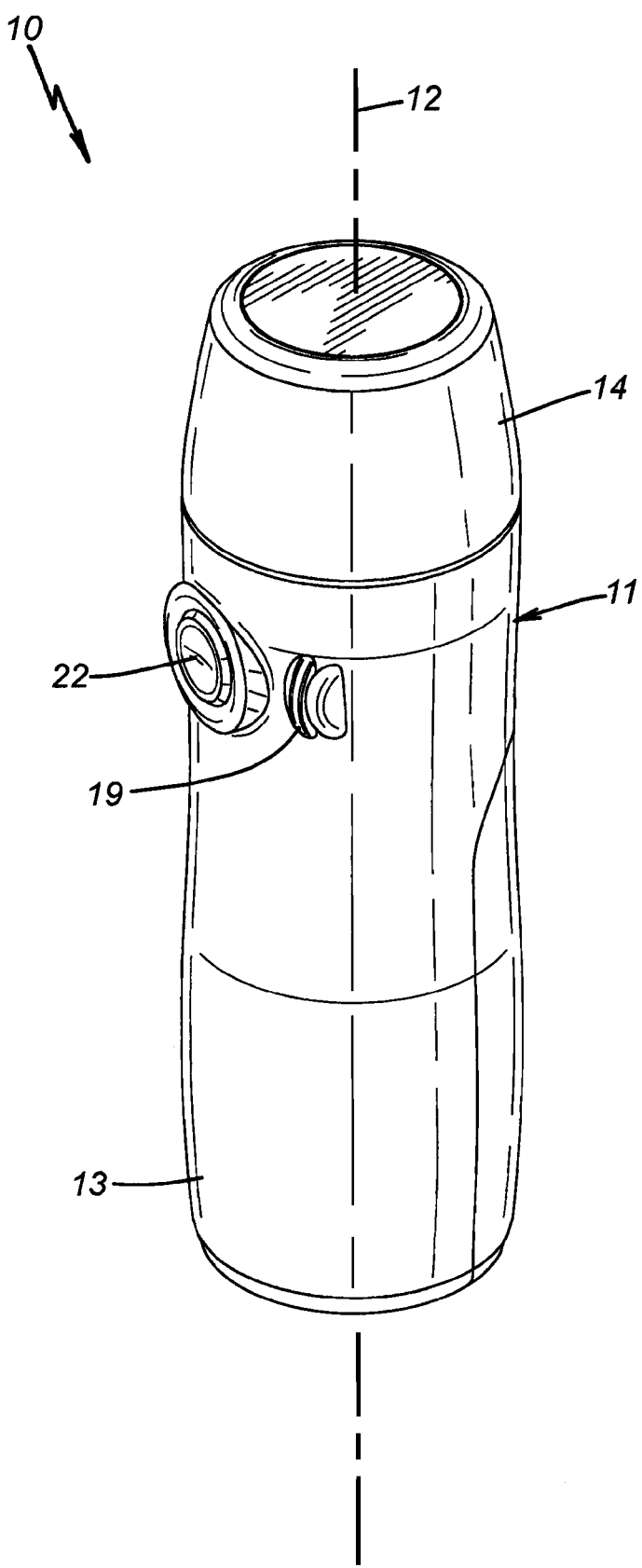
FIG. 1 of the drawings is a first perspective view of an electrolarynx constructed according to the mode switch aspect of the invention, showing the distal or forward end portion of the electrolarynx positioned toward the top of the drawing sheet, a pushbutton side portion (i.e., a control-button side portion) positioned toward the left side of the drawing sheet, and a proximal portion (i.e., a bottom portion) positioned toward the bottom of the drawing sheet.
Figure 2:
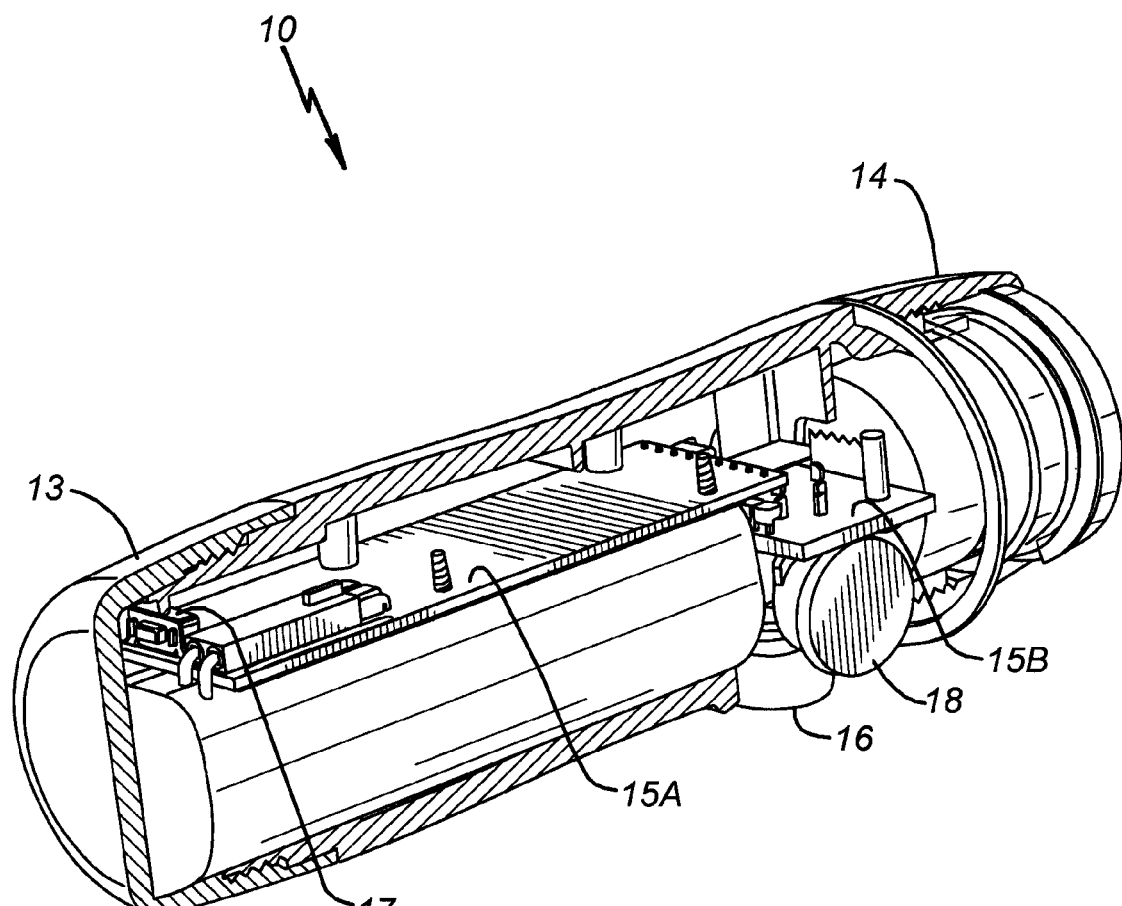
FIG. 2 of the drawings is a second perspective view of the electrolarynx, showing the distal end portion positioned toward the right side of the drawing sheet, the pushbutton side portion positioned toward the bottom of the drawing sheet, and the proximal end portion positioned toward the right side of the drawing sheet.
Figure 3:
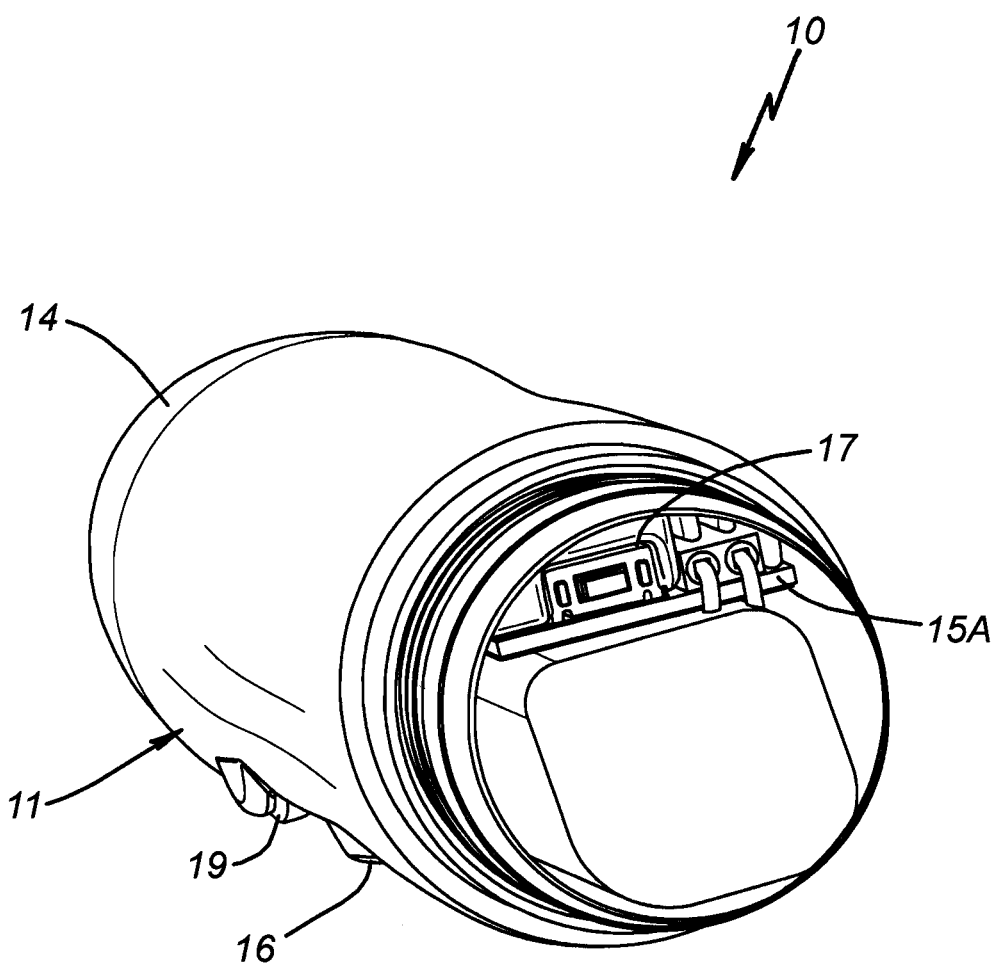
FIG. 3 of the drawings is a third perspective view of the electrolarynx, with the bottom end cap removed so that the mode switch is visible, as viewed facing toward the proximal end portion of the electrolarynx.

FIGS. 1, 2, and 3 of the drawings show an electrolarynx 10 constructed according to the mode switch aspect of the present invention. The electrolarynx 10 may be similar in many respects to the electrolarynxes described in U.S. Pat. Nos. 5,812,681; 6,252,966; 9,031,249; and 9,116,539. Those patents are incorporated herein in their entireties by this reference for all the information they provide.

Generally, the electrolarynx 10 includes a case 11 (FIGS. 1, 2, and 3) that extends along a central axis of elongation 12 of the case 11, between a first or bottom end cap 13 at a proximal or bottom end portion of the case (FIGS. 1 and 2) and a second or top end cap at a distal or forward end portion of the case (FIGS. 1 and 2). The user grasps the case 11, presses the top end cap 14 (i.e., the sound-producing transducer portion at the forward end of the electrolarynx 10) against the outside of their throat in order to introduce an electrolarynx tone to their mouth and throat, and then modulates that tone by holding their breath while varying the shape of the resonant speech cavity and making the usual tongue, teeth, and lip constrictions so as to articulate the modulated tone as human speech.

The case 11 is a handheld component (e.g., a molded-plastic or metal alloy object) having an overall length of about four to five inches measured along the central axis of elongation 12. Of course, that dimension provides an idea of the size of the various components of the illustrated embodiment; the size may vary without departing from the inventive concepts described herein. The case 11 includes a first longitudinally extending section (i.e., a first half) and a second longitudinally extending section (i.e., a second half) that, when fully assembled, are held together by the bottom and top end caps 13 and 14. The assembler person screws the bottom and top end caps 13 and 14 onto the first and second sections, in threaded engagement of the first and second sections, to hold the two halves together. Thus, the term "case" herein means an object such as the case 11, an object that is preferably no longer than about seven inches, with a cross sectional area that is preferably no more than about five to seven square inches.

Figure 4:
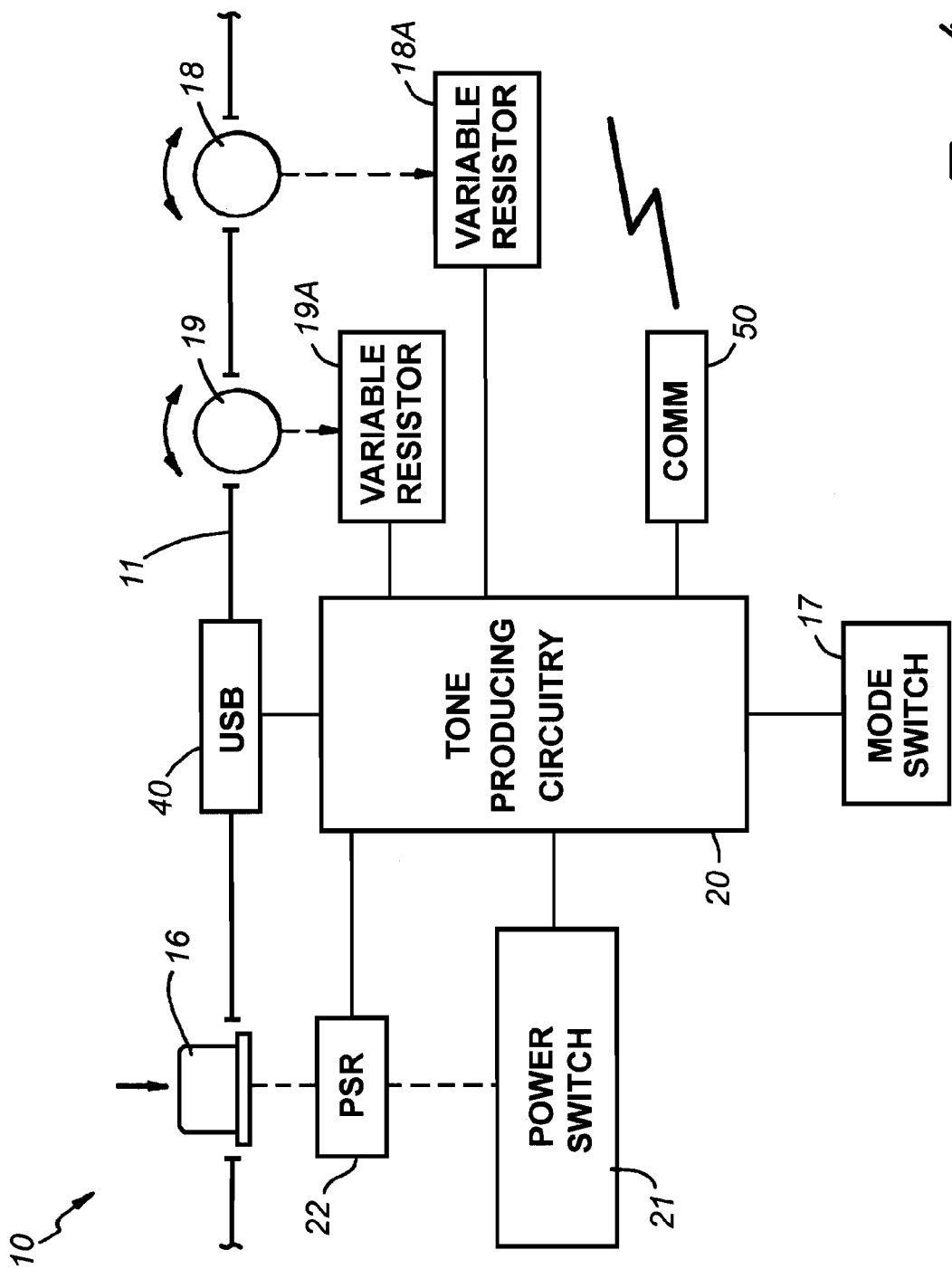
FIG. 4 is a diagrammatic block diagram of the electrolarynx tone-producing circuitry, including the pushbutton, the PSR, and the mode switch.

With the first and second sections fully assembled, the case 11 defines a hollow interior that provides a space for a battery-powered circuit board 15 that is the combination of a first circuit board section 15A and a second circuit board section 15B (FIG. 2). Circuitry on and/or connected to the circuit board 15 includes a switch-activating pushbutton 16 (i.e., a switch-depressing component) that is identified in FIGS. 1 through 5, a mode switch 17 (FIGS. 2 through 5), a frequency-controlling first thumbwheel 18 (FIGS. 2 and 4), and a volume-controlling thumbwheel 19 (FIGS. 1, 3, and 4). The user depresses the pushbutton 16 to turn on power to the electrolarynx 10 so that it produces an electrolarynx tone, while the user operates the thumbwheels 18 and 19 to set a desired frequency and volume of that tone.

FIG. 4 shows the components mentioned above, together with additional components of the electrolarynx 10 that are connected to electronic circuitry identified as "tone-producing circuitry 20." The tone-producing circuitry 20 includes a transducer component for producing the electrolarynx tone. It may take the form of a known type of electromechanical transducer assembly that includes a coil of magnet wire for producing a magnetic field such that it causes a plunger to vibrate against a button-like diaphragm and thereby produce a buzzing electrolarynx sound (i.e., the electrolarynx tone) having an audible fundamental frequency in the speech range of the average human voice (e.g., about 40 Hertz up to about 200 Hertz). Use of a linear motor falls within the broader inventive concepts and the term transducer component herein includes that alternative.

The frequency-controlling first thumbwheel 18 is connected to a first variable resistor 18A that is, in turn, connected to the tone-producing circuitry 20. Similarly, the volume-controlling second thumbwheel 19 is connected to a second variable resistor 19A that is connected to the tone-producing circuitry 20. In operation, the action of the user depressing the pushbutton 16 (e.g., a 0.4-inch diameter pushbutton) activates the switch 21 (i.e., turns on power) with the result that the tone-producing circuitry 20 produces the electrolarynx tone with a thumbwheel-determined value of frequency (TWDF) and thumbwheel-determined level of volume (TWDV) that are determined by the positions of the first and second thumbwheels 18 and 19.

According to the mode switch aspect of the present invention, the tone-producing circuitry 20 is configured to operate in multiple modes of electrolarynx operation. In a first frequency-varying mode (i.e., the first FVM), the tone-producing circuitry 20 enables the user to vary the frequency of the electrolarynx tone from the TWDF within a range of pushbutton-controlled frequencies that is predetermined or indicated by user-inputted settings, doing so by varying pressure on the pushbutton 16 (e.g., similar to the technique described in U.S. Pat. No. 5,812,681). In the first volume-varying mode (i.e., the first VVM), the tone-producing circuitry 20 enables the user to vary the volume of the electrolarynx volume from the TWDV by varying pressure on the pushbutton 16. The user can preselect the first FVM or the first VVM using the mode switch 17 component of the electrolarynx circuitry.

More specifically, the electrolarynx 10 includes a pressure-sensitive resistor (i.e., a PSR 22 in FIG. 4) that is physically coupled to the pushbutton 16 (e.g., interposed between the pushbutton 16 and the switch 21) so that the pressure-sensitive resistor has a resistance value that is dependent on pressure applied by the user to the pushbutton 16. The illustrated pushbutton 16 extends from a user-accessible position on the exterior of the case 11, through the case 11 to the interior of the case 11, where it is mechanically coupled via the PSR 22 to the switch 21. The PSR 22 is a known type of component having a resistance value that varies according to the pressure applied to it; it is commercially available from various sources, including Interlink Electronics, Inc. of Camarillo, Calif., and the term "pressure-sensitive resistor" herein (and the acronym "PSR") mean a resistance component having a resistance value that varies according to the pressure (i.e., the force) applied to that resistor component. Depressing the pushbutton 16 results in pressure against the PSR 22 that varies its resistance. Thus, the user can depress the pushbutton 16 to turn on the electrolarynx tone, and also to vary the resistance of the PSR 22. The tone-producing circuitry 20 responds to variations in the resistance of the PSR 22 by varying the frequency or volume of the electrolarynx tone according to the selected mode of electrolarynx operation.

Preferably, additional modes are provided for also, including, for example, a communications-link mode for enabling control from an external device, and a disabled mode for disabling response of the tone-producing circuitry 20 to the PSR 22. Moreover, five or more modes may be included. At initial power up of the electrolarynx 10 (e.g., by inserting a nine-volt battery), the tone-producing circuitry 20 preferably defaults to the disabled mode mentioned above. Preferably, a mode selected after initial power up is maintained in memory during periods that the electrolarynx 10 is not in use.

The mode switch 17 of the electrolarynx 10 enables a user to select a desired one of multiple modes of operation. The illustrated mode switch 17 is a momentary, normally open, pushbutton switch that the user operates for that purpose, with the tone-producing circuitry 20 responding to each operation of the mode switch 17 by stepping through multiple modes of operation. Other types of user input devices may be used for mode control instead within the broader inventive concepts described herein. For the illustrated mode switch 17, the user depresses it one time to select the first FVM and multiple times to select the first VVM.

Figure 5:
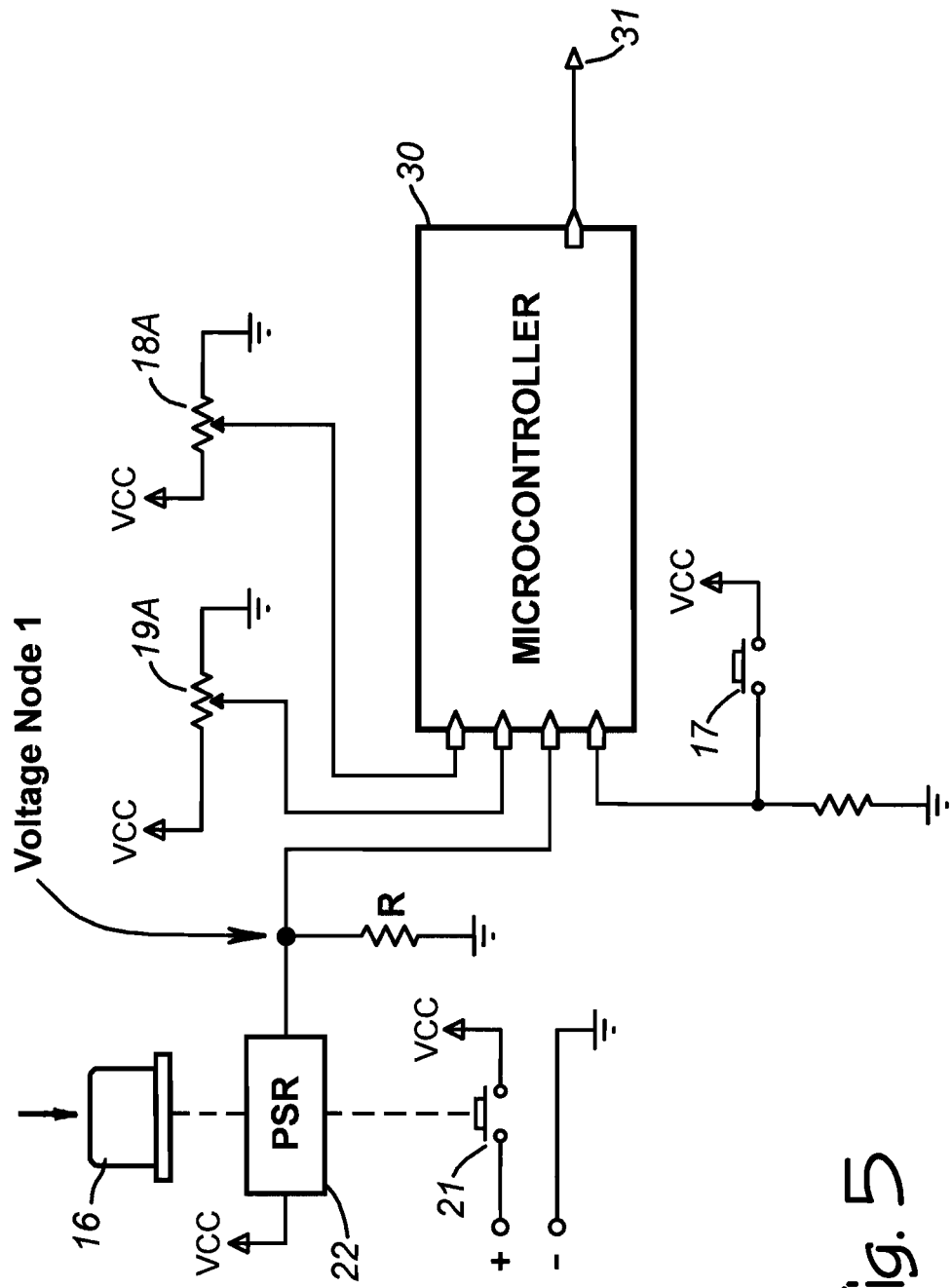
FIG. 5 is a schematic diagram showing connections to a microcontroller component of the tone-producing circuitry.

The tone-producing circuitry 20 in FIG. 4 is configured so that the electrolarynx 10 operates as herein described. In other words, the tone-producing circuitry 20 includes a combination of analog and/or digital circuit components that are interconnected (and programmed where required) to work together and function as stated. FIG. 5 shows the tone-producing circuitry 20 implemented with a microcontroller 30 that controls operation under program control to provide a transducer component drive signal at a line 31 in FIG. 5 that results in the electrolarynx tone. The illustrated microcontroller 30 is, for example, the flash microcontroller having part number PIC16F1824 that is available from Microchip Technology Inc. of Mission Viejo, Calif., and the term "microcontroller" herein means a small electronic computer device (e.g., an integrated circuit containing a processor core and memory) that operates under program control according to the way it has been programmed. The microcontroller 30 is accompanied by suitable support circuitry, including a battery connected to the plus (+) and minus (−) terminals in FIG. 5. It is programmed to function as herein described (e.g., in line with known programming techniques). A USB port 40 (FIG. 4) facilitates communication with the microcontroller 30. Suitable programming for the microcontroller may be created by a programmer in any of various known ways to implement the present invention, including, for example, using a high-level, general purpose programming language (e.g., the commonly used "C" programming language) to produce a source program with the desired features that the programmer compiles and converts to a machine language program file for a manufacturer of the microcontroller to use in loading the programming onto the microcontroller as part of the manufacturing process.

Preferably, the tone-producing circuitry 20 of the electrolarynx 10 is configured to enable the user to set a user-selected one of multiple sensitivity levels for the FVM and VVM operational modes of the electrolarynx 10. In other words, the tone-producing circuitry 20 is configured to respond to variations in PSR resistance with a degree of sensitivity to PSR resistance that the user sets with the mode switch. Depressing the mode button one (1) time after initially powering up the electrolarynx 20, for example, results in the first FVM at a first or "low" FVM sensitivity level (i.e., changes in frequency are relatively less sensitive to variations in PSR resistance). Similarly, depressing the mode button two (2) times results in a second FVM at a second or "low-medium" FVM sensitivity level, depressing it three (3) times results in a third FVM at a third or "high-medium" FVM sensitivity level, and depressing it four (4) times results in a fourth FVM at a fourth or "high" FVM sensitivity level.

For multiple volume-varying modes, depressing the mode button five (5) times results in the first VVM at a first or "low" VVM sensitivity level, and depressing the mode button six (6) times results in a second VVM at a second or "high" VVM sensitivity level. After that, depressing the mode button seven (7) times results in the communications-link mode of electrolarynx operation (i.e., control by an external device via the communications link), and depressing the mode button eight (8) times results in the disabled mode (i.e., the other modes of electrolarynx operation are disabled). For additional depressions of the mode switch, the tone-producing circuitry 20 recycles though the operational modes described above for the mode-switch depressions one through eight, doing it that way until the next initial power-up of the electrolarynx (e.g., battery change), at which time it begins anew as described above for the first mode-switch depression after initial power-on. One alternate embodiment of an electrolarynx constructed according to the invention, however, stores user settings in non-volatile memory so that they are retained for the next power-up of the electrolarynx.

The following summarizes some of the nomenclature used herein for the various frequency-varying and volume-varying modes:

1. The "first frequency-varying mode" is a first FVM in which the tone-producing circuitry varies the frequency of the electrolarynx tone according to variations in the resistance value of the pressure-sensitive resistor, doing so at a first FVM sensitivity to the resistance value of the pressure-sensitive resistor (e.g., a "low" FVM sensitivity level).
2. The "second frequency-varying mode" is a second FVM in which the tone-producing circuitry varies the frequency of the electrolarynx tone according to variations in the resistance value of the pressure-sensitive resistor, doing so at a second FVM sensitivity to the resistance value of the pressure-sensitive resistor (e.g., a "low-medium" FVM sensitivity level).
3. The "third frequency-varying mode" is a third FVM in which the tone-producing circuitry varies the frequency of the electrolarynx tone according to variations in the resistance value of the pressure-sensitive resistor, doing so at a third FVM sensitivity to the resistance value of the pressure-sensitive resistor (e.g., a "high-medium" FVM sensitivity level).
5. The "fourth frequency-varying mode" is a fourth FVM in which the tone-producing circuitry varies the frequency of the electrolarynx tone according to variations in the resistance value of the pressure-sensitive resistor, doing so at a fourth FVM sensitivity to the resistance value of the pressure-sensitive resistor (e.g., a "high" FVM sensitivity level).
6. The "first volume-varying mode" is a first VVM in which the tone-producing circuitry varies the volume of the electrolarynx tone according to variations in the resistance value of the pressure-sensitive resistor, doing so at a first volume-varying-mode (VVM) sensitivity to the resistance value of the pressure-sensitive resistor (e.g., a "low" VVM sensitivity level).
7. The "second volume-varying mode" is a second VVM in which the tone-producing circuitry varies the volume of the electrolarynx tone according to variations in the resistance value of the pressure-sensitive resistor, doing so at a second VVM sensitivity to the resistance value of the pressure-sensitive resistor (e.g., a "high" VVM sensitivity level).

Concerning the communications-link mode of electrolarynx operation, the electrolarynx 10 includes communication circuitry 50 for that purpose (FIG. 4). It communicates, for example, with an external device (not shown) that is not physically connected to the electrolarynx 10. The communication circuitry 50 is connected to the tone-producing circuitry 20 and may use known technology, including, for example, 2.45 GHz radio frequency (RF) communications and/or an infrared (IR) receiver. Frequency and/or volume information are communicated from the external device via the circuitry 50.

From the descriptions provided and those incorporated by reference, a person having ordinary skill in the art (i.e., a PHOSITA) can readily provide suitable circuitry for the communication link. Any of various transmission, reception, and encoding methods may be used, including wire, radio, and infrared. The illustrated communications circuitry 50 may include, for example, an infrared sensor (not shown) that extends through an opening in the case 11 where it receives an infrared signal on which at least one of "on-off information," "frequency information," and "volume information" is encoded. That information is encoded at the external device, for example, in response to a pressure sensor placed proximate an opening in the user's throat through which the user exhales (e.g., a surgical opening called a stoma).

Thus, the mode switch aspect of the present invention provides an electrolarynx having a pushbutton for turning on the electrolarynx tone, a PSR coupled to the pushbutton, tone-producing circuitry for producing variations in attributes of the electrolarynx tone according to variations in the resistance of the PSR, and a mode switch for enabling a user to select the tone attributes affected. Although an exemplary embodiment has been shown and described, one of ordinary skill in the art may make many changes, modifications, and substitutions without necessarily departing from the spirit and scope of the invention. The specific terminology used to describe the exemplary embodiment is not intended to limit the invention; each specific term is intended to include all technical equivalents that operate in a similar manner to accomplish a similar purpose or function.

Nonlinear Frequency Characteristic.

Having described the mode switch aspect of the present invention, this description now turns to the nonlinear frequency characteristic aspect. It improves upon the mode switch aspect by providing a nonlinear frequency characteristic relating force on the pushbutton (i.e., the PSR resistance value) to the frequency of the electrolarynx tone. That nonlinear characteristic is accomplished in one embodiment of the present invention by configuring the tone-producing circuitry so that it applies a shape factor (e.g., a shape factor K) to linearly derived frequency values.

Figure 6:
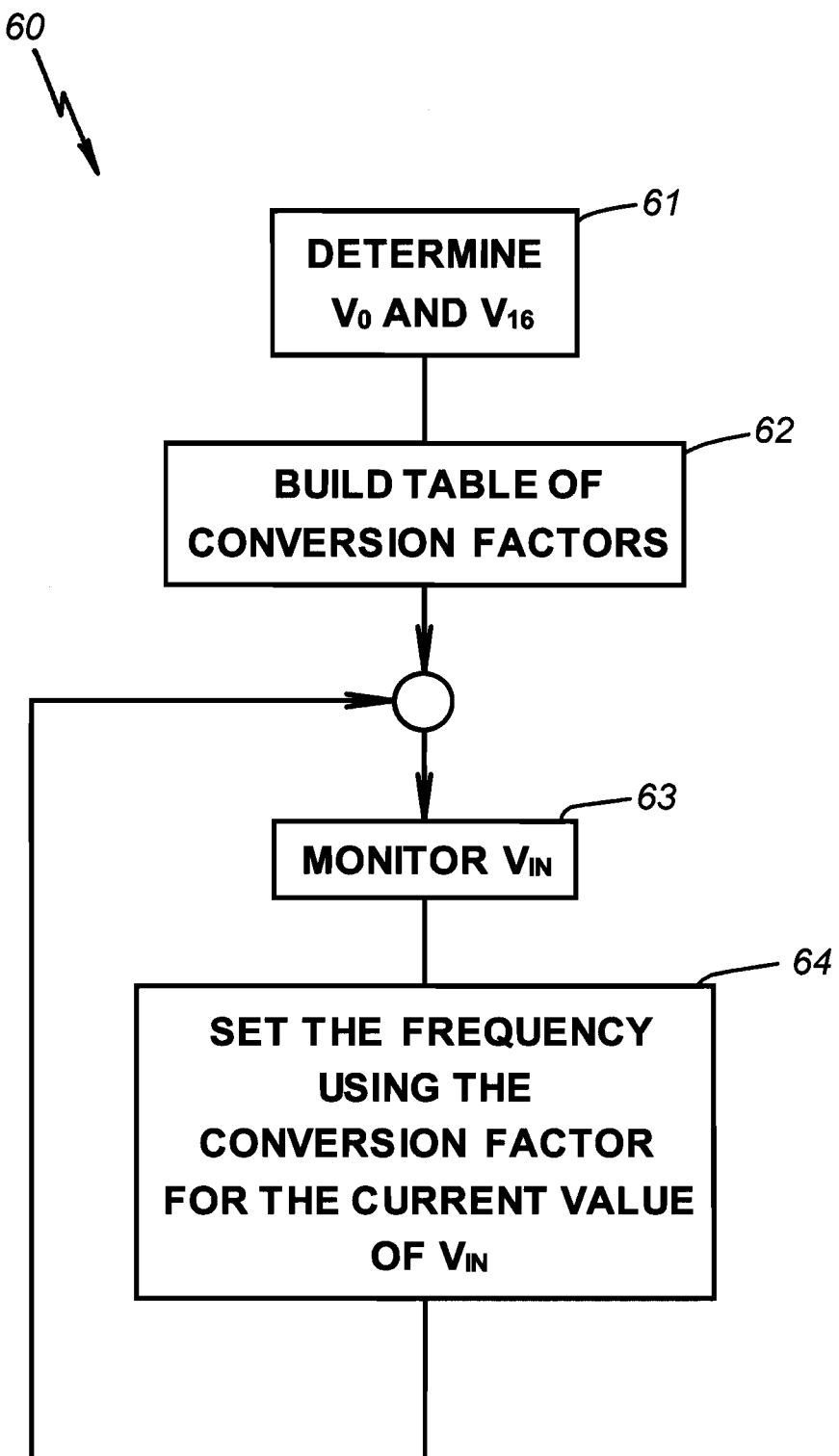
FIG. 6 is a hybrid block-diagram-flow-chart depiction of frequency control as accomplished according to the nonlinear frequency characteristic aspect of the invention.

FIG. 6 provides a diagram 60 as an example of the overall methodology involved in producing a nonlinear frequency characteristic according to the present invention. The manner in which that is accomplished relies on the microcontroller 30 of the tone-producing circuitry; it has been programmed to measure $V_{IN}$ (i.e., the voltage on the node that is identified in FIG. 5 as "Voltage Node 1") as the current value of $V_{IN}$ and to set the current frequency of the electrolarynx tone according to the current value of $V_{IN}$.

The measurement of $V_{IN}$ is made with the analog-to-digital converter (ADC) of the microcontroller 30. As indicated at a block 61 in FIG. 6, the microcontroller 30 of the tone-producing circuitry is programmed to determine $V_{IN}$ for zero force on the PSR 22 (i.e., when the user is not applying force to the pushbutton 16). That value is referred to herein as $V_0$ (i.e., the letter "V" with a subscript "0"). The microcontroller 30 is also programmed to determine $V_{IN}$ for full force on the PSR 22 (i.e., when the user is pushing the pushbutton 16 to a fully depressed position of the pushbutton 16). That value is referred to herein as $V_{16}$ (i.e., the letter "V" with a subscript "16").

Having determined $V_0$ and $V_{16}$, the microcontroller 30 of the illustrated embodiment builds a table of conversion values, including shape factors K, as indicated at a block 62 in FIG. 6. That is done (in the example illustrated by the diagram 60) for a progression of seventeen increments of force on the PSR 22. In doing so, the microcontroller 30 calculates a linear, uniformly spaced apart (i.e., increasing in value uniformly) progression of fifteen values of $V_{IN}$ lying between the values determined in the block 61 for $V_0$ and $V_{16}$. Those fifteen values are referred to hereinafter as $V_1$ (i.e., the letter "V" with a subscript "1") through $V_{15}$ (i.e., the letter "V" with a subscript "15"), with each of the resulting valves of $V_0$ through $V_{16}$ corresponding to a respective one of the seventeen increments of force on the PSR 22 (referred to hereinafter as $P_0$ through $P_{16}$).

In building the table of values, the microcontroller 30 calculates an adjusted value of voltage for each value of $V_{IN}$. Those adjusted values are referred to herein as $V_{ADJ}$ (i.e., the letter "V" with a subscript "ADJ"). The value of $V_{ADJ}$ corresponding to each value of $V_{IN}$ (i.e., for each of $V_0$ through $V_{16}$) is calculated to be $V_{IN}$ reduced by the value $V_0$, with the result that the values of $V_{ADJ}$ range from zero (corresponding to $V_0$) to the value of $V_{16}$ reduced by the value of $V_0$ (corresponding to $V_{16}$). The microcontroller 30 is programmed to use a current voltage ($V_{ADJ}$) appearing across the pressure-sensitive resistor as an indication of a current resistance value of the pressure-sensitive resistor. Based upon the foregoing, the microcontroller 30 completes the table of conversion values, with seventeen shape factors K (i.e., $K_0$ through $K_{16}$), and stores them in memory for use in real time conversion to a nonlinear frequency characteristic. In other words, the microcontroller is programmed to determine the shape factors (K), each of which corresponds to a respective one of a plurality of incremental increases in the resistance value (i.e., increases that correspond to the seventeen increments of force ($P_0$ through $P_{16}$) on the PSR 22.

Instead of building and storing a table of conversion values, however, a person having ordinary skill in the art can, based upon the description provided herein, readily program the microcontroller 30 to compute table values at the time they are needed (e.g., periodically or whenever a change in $V_{IN}$ occurs). The example illustrated in the diagram 60, however, uses a table of values that is stored in the memory of the microcontroller 30. As indicated at a block 63 in FIG. 6, the microcontroller 30 proceeds to monitor the value of $V_{IN}$. As changes in $V_{IN}$ occur, the microcontroller 30 changes the electrolarynx tone frequency accordingly (as indicated at a block 64) using shape factors K to result in a nonlinear frequency characteristic relative to the force on the PSR 22. After setting the frequency that way to reflect the current value of $V_{IN}$, the microcontroller 30 continues to monitor $V_{IN}$, as indicated by the return arrow to the block 63.

The Equation 1 in FIG. 7 provides an example of how the microcontroller 30 computes the shape factors K (i.e., shape factors $K_0$ through $K_{16}$) for the illustrated embodiment of the present invention. As indicated by Equation 1, the shape factor K (expressed as a percentage value) is calculated, for each of the seventeen increments of force on the PSR 22 (i.e., $P_0$ through $P_{16}$), to be equal to the product of one hundred (100) and the illustrated ratio. The letter "X" in that ratio represents one of the seventeen pushbutton pressure increments (i.e., $P_0$ through $P_{16}$) that correspond to respective ones of the seventeen values of $V_{IN}$ (i.e., $V_0$ through $V_{16}$). The "Scale" parameter in that ratio represents a desired amount of nonlinearity.

Any of various shape factors may be used to achieve a desired nonlinear frequency characteristic within the broader inventive concepts of the present invention, and such shape factors may be determined by calculating them using a suitable equation or by setting them empirically, or otherwise. Equation 1, however, gives a reasonable approximation to a logarithmic curve, and the Scale parameter can be used to set the direction and depth of the resulting curve. Setting the Scale parameter to zero (i.e., Scale=0) results in a straight line; setting it greater than zero (i.e., Scale>0) results in a curve that is shallow at low values (less sensitivity to changes in force on PSR 22) and steep at high values; setting it less than zero (i.e., Scale<0) result in a curve that is steep at low values (greater sensitivity to changes in force on the PSR 22) and shallow at high values.

FIG. 8 illustrates the Table A as an example of a table of values having seventeen values of shape factor K in the column headed with "Shape Factor K" (i.e., $K_0$=0.00% through $K_{16}$=100.00% corresponding to $P_0$ through $P_{16}$). The microcontroller 30 determined those values of shape factor K using Equation 1 with a Scale parameter greater than zero (i.e., Scale>0). Table A also includes table values of $V_{IN}$ corresponding to $P_0$ through $P_{16}$ in a column headed "ADC Voltage $V_{IN}$" (i.e., $V_0$=1.65 through $V_{16}$=3.30), along with table values of $V_{ADJ}$ corresponding to $P_0$ through $P_{16}$ in a column headed "ADC Voltage $V_{IN}$" (i.e., 0.00 volts through 1.65 volts). In addition, Table A presents table values of $F_L$ (i.e., the frequencies for a linear frequency characteristic over a pushbutton-controlled frequency range of 50.00 Hertz to 150.00 Hertz that is predetermined or specified by user settings), each such table value corresponding to a respective one of $P_0$ through $P_{16}$. Table A also presents corresponding table values of $V_K$ (i.e., the shaped voltage reflecting the shape factor K applied to the corresponding value of $V_{ADJ}$), and corresponding table values of $F_K$ (the shaped frequency reflecting the shape factor K applied to the corresponding value of $F_L$).

In determining values as shown in Table A, the microcontroller 30 first uses the ADC to determined $V_{IN}$ corresponding to $P_0$ (i.e., $V_0$=1.65 volts) and $V_{IN}$ corresponding to $P_{16}$ (i.e., $V_{16}$=3.30 volts). Using those values for $V_0$ and $V_{16}$, the microcontroller 30 determines the remaining fifteen values of $V_2$ through $V_{15}$ in order to produce linear progression of seventeen values of $V_{IN}$ (i.e., $V_0$ through $V_{16}$). Next, the microcontroller determines the illustrated seventeen values of $V_{ADJ}$ (e.g., the 0.00 volts through 1.65 volts shown in Table A), doing so by reducing the values of $V_0$ through $V_{15}$ by the 1.65-volt value of $V_{IN}$ to produce a linear progression of seventeen values of $V_{ADJ}$. Having determined those values, the microcontroller 30 sets the current frequency of the electrolarynx tone according to the current value of $V_{IN}$ by applying the corresponding shape factor K to the corresponding value of $F_L$, interpolating values where appropriate (e.g., straight line interpolation).

As an example of setting the current frequency in line with the present invention using the values presented in Table A, suppose that the current value of $V_{IN}$ at the Voltage Node 1 identified in FIG. 5 is determined by the ADC to be 2.0 volts (i.e., a value between the $V_3$=1.96 table value of $V_{IN}$ corresponding to $P_3$ and the $V_4$=2.06 table value of $V_{IN}$ corresponding to $P_4$). The microcontroller 30 first reduces that current 2.0-volt value of $V_{IN}$ by 1.65 volts to a value of 0.35 volts as the adjusted current value of $V_{ADJ}$, and then proceeds to set the current frequency $F_K$ accordingly.

Inasmuch as the 0.35-volt adjusted current value of $V_{ADJ}$ lies between the 0.31-volt table value of $V_{ADJ}$ corresponding to $P_3$ and the 0.41-volt table value of $V_{ADJ}$ corresponding to $P_4$, the microcontroller 30 interpolates between the 0.50% table value of the shape factor K corresponding to $P_3$ and the 1.25% table value of the shape factor K corresponding to $P_4$ accordingly (e.g., a linear interpolation) to give a currently operative shape factor K of 0.80%. Applying that 0.80% interpolated shape factor to the 0.35-volt adjusted current value of $V_{ADJ}$ (i.e., applied by multiplying 0.35 by 0.008) yields a 0.0028-volt current value of the shaped voltage $V_K$ (corresponding to the current 2.0-volt value of $V_{IN}$). Similarly, a linear interpolation between the 50.19-Hertz table value of $F_K$ corresponding to $P_3$ and the 50.62-Hertz table value of $F_K$ corresponding to $P_4$ gives a 50.36-Hertz interpolated value for the current shaped frequency of the electrolarynx tone (corresponding to the current 2.0-volt value of $V_{IN}$). In other words, the microcontroller 30 is programmed to interpolate between two shape factors (K) in order to produce an intermediate shape factor. The tone-producing circuitry 20 (FIG. 4) with its microcontroller 30 then produces the electrolarynx tone as predetermined for the current value of the shaped frequency so determined, doing so in line with the above explanation.

Summarizing the nonlinear frequency characteristic aspect of the present invention, the tone-producing circuitry 20 varies the pushbutton-controlled frequency of the electrolarynx tone as a nonlinear function of the force applied to the pushbutton 16 (i.e., a nonlinear function of the PSR 22 resistance value). The microcontroller 30 is preferably programmed to accomplish that result as provided for by the table values in Table A, so that less sensitivity to applied force results at the low end of the pushbutton-controlled frequency range, thereby facilitating low frequency adjustments by a user when the user is only lightly pressing the pushbutton 16. In other words, the microcontroller component of the tone-producing circuitry is programmed to vary the frequency of the electrolarynx tone so that the frequency of the electrolarynx tone is related to the resistance value of PSR 22 by a nonlinear function, preferably over the entire pushbutton-controlled frequency range, and the illustrated embodiment does so to result in reduced sensitivity to the force a user applies to the pushbutton 16 at the low end of the pushbutton-controlled frequency range.

Of course, it is not necessary to fully populate a table of values such as the Table A in order to implement the present invention. The illustrated full Table A is simply provided as an aid in explaining the methodology of the present invention. A programmer may, instead, simply store in memory, or program the microcontroller to calculate, various values of the shape factor K that provide a desired nonlinear frequency characteristic. Depending on the capabilities of the microcontroller used, and inasmuch as the maximum and minimum values of $V_{IN}$ and $F_L$ are known parameters (or readily ascertained), a current value of the linear frequency $F_L$ (i.e., the instantaneous value of $F_L$) may be calculated in real time as a function of the current value of the ADC voltage $V_{IN}$ (i.e., the instantaneous value of $V_{IN}$) and those known parameters (e.g., a continuous function over the range of the voltage $V_{IN}$). Moreover, the shape factor K to be applied to the current or instantaneous value of $F_L$ (in order to yield the current or instantaneous value of the shaped frequency $F_K$) may be calculated in real time also (e.g., as a continuous function over the range of $F_L$).

Stated another way, the microcontroller 30 is programmed to determine a current value of frequency ($F_K$) as a function of a current voltage ($V_{ADJ}$) appearing across the pressure-sensitive resistor, and to determine a current shape factor (K) as a function of the current voltage ($V_{ADJ}$). In other words, the microcontroller 30 is programmed to determine a current frequency ($F_L$) of a linear frequency characteristic relating frequency to the resistance value of the pressure-sensitive resistor, and to apply a shape factor (K) to said current frequency ($F_L$) in order to determine a current frequency ($F_K$) of a nonlinear frequency characteristic relating frequency to the resistance value of the pressure-sensitive resistor.

Based upon the foregoing description and claims herein, one of ordinary skill in the art can readily implement the present invention with many changes, modifications, and substitutions to the illustrated embodiment without necessarily departing from the spirit and scope of the present invention. The specific terminology used to describe the illustrated embodiment is not intended to limit the invention; each specific term is intended to include all technical equivalents that operate in a similar manner to accomplish a similar purpose or function.

Battery Status.

One improvement to the electrolarynx described above relates to battery status. When using a standard alkaline or NiMH 9-volt battery, for example, it is very easy to tell when the battery needs charging. The voltage drops as the battery gets weaker. For a 9-volt lithium battery, however, the voltage drop is less noticeable, and when the battery hits a "dead" status (i.e., charge fully depleted), the battery suddenly cuts out without warning. Or, for a smaller voltage battery (e.g., AA battery or batteries, or a single cell lithium battery at 3.7 volts) in combination with a voltage step-up circuit, the step-up circuit will mask the status of the battery that is nearly ready for charging. Some users are very concerned that when using a lithium battery, they may lose their voice because the electrolarynx device just cuts out without warning. So, the user will often charge the battery far more often than was really necessary.

A solution to the above problem is achieved according to yet another inventive aspect by having the tone-producing circuitry (i.e., the microcontroller) read battery voltage when the electrolarynx turns on, and then calculate battery "Charge Status." A "charge-status" calculating chip may also be used to provide that data. If the Charge Status of the battery is below a certain threshold (e.g., 75% charge status, although that value may vary depending on requirements), then the "Maximum Volume" will be reduced (e.g., to 80% of normal max volume). When the microcontroller detects a low battery (i.e., the Charge Status is below said threshold), the "Full Volume" duty cycle will become 15%, thus limiting how loud the electrolarynx tone is (i.e. under normal use, the duty cycle will be 20% at full volume). This gives the user an audible warning that the battery requires charging, doing so before the electrolarynx just stops working. It also has the benefit of extending the life of the battery, since the battery will not be drained as fast. An alternate warning sound can be generated, such as ramping the volume up over time (e.g., over about 500 milliseconds) so that the audible warning is still there, but the Maximum Volume is still maintained.

What is claimed is:

1. An electrolarynx, comprising:
a case;
tone-producing circuitry on the case for producing an electrolarynx tone having a frequency and a volume;
a power switch on the case for turning on power to the tone-producing circuitry;
a pushbutton on the case for enabling a user to activate the power switch;
a pressure-sensitive resistor on the case that is physically coupled to the pushbutton so that the pressure-sensitive resistor has a resistance value such that said resistance value is dependent on pressure applied by the user to the pushbutton; and
a microcontroller portion of the tone-producing circuitry that is programmed to control the frequency of the electrolarynx tone over a pushbutton-controlled range of frequencies according to the resistance value of the pressure-sensitive resistor, said pushbutton-controlled range of frequencies extending from a minimum frequency to a maximum frequency;
wherein the microcontroller is programmed to vary the frequency of the electrolarynx tone between said minimum frequency and said maximum frequency as a nonlinear function of the resistance value of the pressure-sensitive resistor; and wherein the microcontroller is programmed to determine a current frequency ($F_L$) of a linear frequency characteristic relating frequency to the resistance value of the pressure-sensitive resistor, and to apply a shape factor (K) to said current frequency ($F_L$) in order to determine a current frequency ($F_K$) of a nonlinear frequency characteristic relating frequency to the resistance value of the pressure-sensitive resistor.

2. An electrolarynx as recited in claim 1, wherein the microcontroller is programmed to vary the frequency of the electrolarynx tone according to the resistance value of the pressure-sensitive resistor in order to achieve reduced sensitivity at and near the minimum frequency.

3. An electrolarynx as recited in claim 1, wherein the microcontroller is programmed to determine a current voltage ($V_{ADJ}$) appearing across the pressure-sensitive resistor as an indication of a current resistance value of the pressure-sensitive resistor.

4. An electrolarynx as recited in claim 1, wherein the microcontroller is programmed to determine a plurality of shape factors (K), each of which plurality of shape factors (K) corresponds to a respective one of a plurality of incremental increases in the resistance value of the pressure-sensitive resistor.

5. An electrolarynx as recited in claim 4, wherein the microcontroller is programmed to interpolate between two of said plurality of shape factors (K) in order to produce an intermediate shape factor.

6. An electrolarynx as recited in claim 1, wherein the microcontroller is programmed to determine a current value of frequency ($F_K$) as a function of a current voltage ($V_{ADJ}$) appearing across the pressure-sensitive resistor.

7. An electrolarynx as recited in claim 1, wherein the microcontroller is programmed to determine a current shape factor (K) as a function of a current voltage ($V_{ADJ}$) appearing across the pressure-sensitive resistor.

8. An electrolarynx comprising:
a case;
tone-producing circuitry on the case for producing an electrolarynx tone having a frequency and a volume;
a power switch on the case for turning on power to the tone-producing circuitry;
a pushbutton on the case for enabling a user to activate the power switch;
a pressure-sensitive resistor on the case that is physically coupled to the pushbutton so that the pressure-sensitive resistor has a resistance value such that said resistance value is dependent on pressure applied by the user to the pushbutton; and
a microcontroller portion of the tone-producing circuitry that is programmed to control the frequency of the electrolarynx tone over a pushbutton-controlled range of frequencies according to the resistance value of the pressure-sensitive resistor, said pushbutton-controlled range of frequencies extending from a minimum frequency to a maximum frequency;
wherein the microcontroller is programmed to vary the frequency of the electrolarynx tone between said minimum frequency and said maximum frequency as a nonlinear function of the resistance value of the pressure-sensitive resistor;
wherein the electrolarynx includes a mode switch on the case that is electrically connected to the tone-producing circuitry;

wherein the tone-producing circuitry is configured to operate in a first frequency-varying mode in which the tone-producing circuitry varies the frequency of the electrolarynx tone according to variations in the resistance value of the pressure-sensitive resistor, doing so at a first frequency-varying mode sensitivity to the resistance value of the pressure-sensitive resistor;

wherein the tone-producing circuitry is configured to operate in a first volume-varying mode in which the tone-producing circuitry varies the volume of the electrolarynx tone according to variations in the resistance value of the pressure-sensitive resistor, doing so at a first volume-varying mode sensitivity to the resistance value of the pressure-sensitive resistor; and wherein the tone-producing circuitry is configured to enable a user to select a desired mode of electrolarynx operation by operation of the mode switch.

9. An electrolarynx, comprising:
a case;
tone-producing circuitry on the case for producing an electrolarynx tone having a frequency and a volume;
a power switch on the case for turning on power to the tone-producing circuitry;
a pushbutton on the case for enabling a user to activate the power switch;
a pressure-sensitive-resistor on the case that is physically coupled to the pushbutton so that the pressure-sensitive resistor has a resistance value such that said resistance value is dependent on pressure applied by the user to the pushbutton; and
a mode switch on the case that is electrically connected to the tone-producing circuitry;
wherein the tone-producing circuitry is configured to operate in a first frequency-varying mode in which the tone-producing circuitry varies the frequency of the electrolarynx tone according to variations in the resistance value of the pressure-sensitive resistor, doing so at a first frequency-varying mode sensitivity to the resistance value of the pressure-sensitive resistor;
wherein the tone-producing circuitry is configured to operate in a first volume-varying mode in which the tone-producing circuitry varies the volume of the electrolarynx tone according to variations in the resistance value of the pressure-sensitive resistor, doing so at a first volume-varying mode sensitivity to the resistance value of the pressure-sensitive resistor;
wherein the tone-producing circuitry is configured to enable a user to select a desired mode of electrolarynx operation by operation of the mode switch;
wherein the electrolarynx includes a microcontroller portion of the tone-producing circuitry that is programmed to control the frequency of the electrolarynx tone according to the resistance value of the pressure-sensitive resistor; and
wherein the microcontroller is programmed to vary the frequency of the electrolarynx tone as a nonlinear function of the resistance value of the pressure-sensitive resistor.

10. An electrolarynx, as recited in claim 9, wherein:
the electrolarynx includes communications circuitry for providing a communications link with a device that is not physically connected to the electrolarynx;
the tone-producing circuitry is configured to operate in a communications-link mode in which the tone-producing circuitry responds to control information received via the communications link; and wherein the tone-producing circuitry is configured to enable a user to select the communications-link mode by operation of the mode switch.

11. An electrolarynx, as recited in claim 9, wherein:
the tone-producing circuitry is configured to operate in a disabled mode in which the frequency-varying mode, the volume-varying mode, and the communications-link mode are disabled; and
wherein the tone-producing circuitry is configured to enable a user to select the disabled mode by operation of the mode switch.

12. An electrolarynx, as recited in claim 9, wherein:
the tone-producing circuitry is configured to operate in multiple modes of electrolarynx operation; and
the tone-producing circuitry is configured to respond to a predetermined number of mode switch closures in setting a corresponding user-selected mode of electrolarynx operation.

13. An electrolarynx, as recited in claim 9, wherein the tone-producing circuitry is configured to operate in multiple frequency-varying modes such that each of said multiple frequency-varying modes has a different frequency-varying mode sensitivity to the resistance value of the pressure-sensitive resistor; and the tone-producing circuitry is configured to operate in a user-selected one of said multiple frequency-varying modes according to operation of the mode switch.

14. An electrolarynx, as recited in claim 9, wherein the tone-producing circuitry is configured to operate in multiple volume-varying modes such that each of said multiple volume-varying modes has a different volume-varying mode sensitivity to the resistance value of the pressure-sensitive resistor; and the tone-producing circuitry is configured to operate in a user-selected one of said multiple volume-varying modes according to operation of the mode switch.

15. An electrolarynx, as recited in claim 9, wherein the tone-producing circuitry is configured to operate in multiple modes of electrolarynx operation according to operation of the mode switch so that (1) a first closure of the mode switch sets the first frequency-varying mode at the first frequency-varying mode sensitivity, (2) a second closure of the mode switch sets a second frequency-varying mode at a second frequency-varying mode sensitivity, (3) a third closure of the mode switch sets a third frequency-varying mode at a third frequency-varying mode sensitivity, (4) a fourth closure of the mode switch sets a fourth frequency-varying mode at a fourth frequency-varying mode sensitivity, (5) a fifth closure of the mode switch sets the first volume-varying mode at the first volume-varying mode sensitivity (6) a sixth closure of the mode switch sets a second volume-varying mode at a second volume-varying mode sensitivity, (7) a seventh closure of the mode switch sets the communications-link mode, and (8) an eighth closure of the mode switch sets the disabled mode.

16. An electrolarynx, as recited in claim 9, wherein:
the electrolarynx includes a battery that provides power to the tone-producing circuitry;
the tone-producing circuitry is configured to produce the electrolarynx tone at various volume levels up to a Maximum Volume;
the tone-producing circuitry is configured to calculate a Charge Status of the battery; and
the tone-producing circuitry is configured to reduce the level of the Maximum Volume according to the Charge Status of the battery.

17. An electrolarynx, as recited in claim 16, wherein the tone-producing circuitry is configured to produce a warning sound if the battery Charge Status of the battery falls below a predetermined level.

* * * * *